(12) United States Patent
Wong et al.

(10) Patent No.: US 6,875,185 B2
(45) Date of Patent: Apr. 5, 2005

(54) INTEGRATED CONFIRMATION SAMPLE IN A BODY FLUID TEST DEVICE AND METHOD OF USING

(75) Inventors: Raphael C. Wong, Irvine, CA (US); Dequn Wang, San Diego, CA (US)

(73) Assignee: Branan Medical Corporation, Irvine, CA (US)

( * ) Notice: Subject to any disclaimer, the term of this patent is extended or adjusted under 35 U.S.C. 154(b) by 19 days.

(21) Appl. No.: 10/208,574

(22) Filed: Jul. 29, 2002

(65) Prior Publication Data

US 2004/0019301 A1 Jan. 29, 2004

(51) Int. Cl.[7] .............................. A61B 5/00; B65D 81/00
(52) U.S. Cl. ............................ 600/584; 422/58; 422/99
(58) Field of Search .................................. 600/573, 584; 422/56, 58–60, 99, 104; 435/287.7, 287.9, 288.7, 970; 436/518, 524, 530, 541, 807

(56) References Cited

U.S. PATENT DOCUMENTS 6,248,598 B1 * 6/2001 Bogema ..................... 436/518
6,303,081 B1 * 10/2001 Mink et al. .................. 422/61
6,365,417 B1 * 4/2002 Fleming et al. ............. 436/514
6,372,516 B1 * 4/2002 Sun ............................ 436/518
6,464,939 B1 * 10/2002 Bachand et al. ............. 422/58
2001/0023324 A1 * 9/2001 Pronovost et al. .......... 600/582

* cited by examiner

*Primary Examiner*—Charles Marmor
(74) *Attorney, Agent, or Firm*—Myers Dawes Andras & Sherman LLP; Vic Lin

(57) ABSTRACT

A lateral flow immunoassay contact chemical test device and method integrates sample collection, prescreen testing, and confirmation sample collecting and storing with a single device and a minimum of steps. While particularly advantageously used with an oral fluid sample absorbed directly from a person's mouth, (in which constant monitoring of a collection process is made possible), the test device may be used with any of a variety of sample fluids. Prescreen testing and confirmation testing are performed on a single sample. Prescreen testing is performed by a lateral flow assay. The sample collection pad is subsequently separated from the wicking path to prevent continued migration from, and backflow into the sample collection pad, so that the confirmation sample is preserved in the sample collection pad. A multitude of antigens can be detected with a single device.

30 Claims, 6 Drawing Sheets

INTEGRATED CONFIRMATION SAMPLE IN A BODY FLUID TEST DEVICE AND METHOD OF USING

BACKGROUND OF THE INVENTION

1. Field of the Invention

The invention relates generally to all types of body fluid test devices and methods, and specifically to oral drug use tests.

2. Description of Prior Art and Related Information

Some of the most common body fluids tests comprise immunoassay tests. Immunoassay tests are generally based on the competition between a target antigen and a known amount of antigen derivative. The antigen derivative is generally the antigen or an appropriate analog thereof. A predetermined amount of a specific antibody provides a limited number of binding sites for which the antigen and antigen derivative compete. These types of immunoassays have been used extensively in urinalysis devices and methods.

Some immunoassay devices are lateral flow devices, and the antibodies are movably supported on a solid support such as a porous pad. The antigen derivatives are deposited as immobilized indicator lines downstream of the antibodies, whereby the target antigens in a fluid sample flow laterally as a liquid matrix by capillary action through the solid support. In this case, the antibodies are normally colored for visual indication. The fluid sample carries the antibodies downstream towards the indicator lines of immobilized antigen derivatives while a reaction takes place between the target antigens and the antibodies. Any antibodies that have not reacted with the antigen in the sample bind to the antigen derivatives at the indicator lines. When little or no target antigen is present in the sample, most or all of the colored antibodies are carried downstream to the indicator lines of the immobilized antigen derivatives. At the immobilized antigen derivatives, the colored antibodies bind together with the antigen derivatives in such concentrations that the colorant of the antibodies becomes readily visible. It is also known that the antigen derivatives and the antibodies can be interchanged. That is, the antigen derivatives can be labeled with colorant and movably placed in the solid support while the antibodies are placed as immobilized deposited indicator lines downstream.

A majority of the immunoassay test devices and methods of the past are for urinalysis. While urinalysis testing has many advantages and is a well accepted type of testing, urinalysis does have certain drawbacks.

Urinalysis devices have perhaps been popular because of the relative ease of obtaining the sample as compared to taking blood. Historically, urine samples could be taken with little or no contamination to the samples. However, in the case of abused drug tests, there are added concerns of intentional adulteration of the sample by the donor.

Urinalysis has always had the drawback of requiring the handling of urine, which many operators find objectionable. Another drawback to utilizing urine samples is that the kidneys function as a filter for blood. Hence, the urine samples vary with physiological and pathological status, and do not closely resemble the dynamic chemical concentrations in the blood.

Typically, urinalysis utilizes large sample sizes. As such, urinalysis often has the disadvantage that the sample containers take up much space. The larger sample sizes typically provided by urinalysis sampling are advantageous for some tests. For example, abused drug testing requires a confirmation test in addition to a prescreening test. Therefore, the overall sample typically must be larger. In some instances however, the collected sample is insufficient for both an initial prescreening test and the confirmation test. In such cases, a second sample is needed. However, the results from the second sample may not be properly comparable to the prescreening test results from the original sample because the second sample most likely does not have the same constitution as the original sample, which could lead to legal challenge by the donor. Therefore, sampling for both the prescreen and confirmation testing must be repeated on a common sample.

A drawback to the conventional lateral flow immunoassay urinalysis devices is that they require a measure of privacy during sample collection. As such, the extent of contamination to the sample cannot be adequately monitored during sample collection. In order to overcome this deficiency, some government agencies have established the policy of having an attendant of the same sex observe during sample collection in order to identify accidental or intentional contamination of the sample. These provisions, of course, are embarrassing for the donor and the observer and add to the cost of testing.

In light of the many drawbacks of urinalysis, it is clear that viable alternatives for testing other body fluids may be of great interest. For example, immunoassays on oral fluids are particularly advantageous in overcoming the need for privacy during sampling in urinalysis testing.

A few devices have been developed for lateral flow testing of oral fluids. Even though the devices developed for oral fluid testing have overcome some drawbacks of conventional urinalysis and including some drawbacks associated with lateral flow urinalysis, the oral immunoassay test devices still have deficiencies of their own. For example, the lateral flow immunoassay test devices for oral fluid have means for both collection and prescreen testing of oral fluid. However, they are deficient in providing structure for preserving a portion of the sample for confirmation testing in a single device. Furthermore, these devices are deficient in teaching a method of preserving a portion of the sample for confirmation testing.

Alternatively stated, the devices of the past require a cumbersome amount of separate equipment and steps to accomplish collecting, prescreening, and confirmation testing of samples. This is due to the fact that confirmation testing is not provided for by the oral fluid test devices and due to the other drawbacks set forth above for urinalysis devices and methods.

A drawback of immunoassay testing of oral fluids is that they generally have lower concentrations of antigens to be detected. Furthermore, the viscous nature of oral fluid impedes flow of the oral fluid to or around any reagent. Another drawback of the oral test devices and methods of the past is that the sample size is small and only serves for a prescreen test. Yet government regulations require confirmation testing before relying on a positive result of a prescreen test. Thus, if a confirmation test is desired, then a second sample has to be taken.

Taking two separate samples for prescreening and confirmation is problematic since it is not clear whether both samples will contain the same substances, as discussed with regard to taking a second urinalysis sample above. A difference in the contents of a second sample from a first sample is more probable if any time lapses between sampling, for example when a prescreen test is positive and the subject person has to be called back for a second sample. Furthermore, getting a second sample requires added time and inconvenience. The limited use of immunoassays of oral fluids is evidence that oral test devices and methods of the past have not found ways to take advantage of the inherent positive aspects associated with oral tests. Apparently, the devices of the past have not provided adequate solutions to the problems discussed above.

The devices of the past also fall short in providing reagents for both adulterant chemicals added to the body fluid at the time of testing and antigens that were present in the body fluid prior to a time of testing. Additionally, the devices of the past are deficient in providing a large number of reagents in order to detect multiple antigens in the sample with a single test.

Due to the many deficiencies and drawbacks of the test devices of the past, it is apparent that there is in need in the art for a simple device that incorporates as much of the required testing as possible in the single device, and that reduces the number of steps required. In addition, there are additional needs for a viable oral testing device and solutions to the other deficiencies set forth above.

SUMMARY OF THE INVENTION

The instant device and method overcome the deficiencies of the past and fill the needs set forth above by a simple test device that can be made small in size and that can be easily and efficiently used.

The test device is particularly for determining a presence of of one or more target substances in oral fluid and integrates a prescreen test sample and a confirmation test sample collection with the single device.

For purposes of clarity the target substances are referred to herein by the exemplary term "antigens", the substances placed in the device for simulating the antigents are referred to as "antigen derivatives", and the substances that are conjugates of the antigens and antigen derivatives are referred to as "antibodies". It is to be expressly understood that the terms antigen/antibody refer to a particular type of target substance and its binding conjugate. Analogous terms can be used in place of each of these terms as can be appreciated from the disclosures of U.S. Pat. No. 6,365,417 to Fleming et al. and U.S. Pat. No. 6,248,598 to Bogema, which are incorporated herein by reference. For example, the term antigen could be replaced by analyte, target substance; or ligand, and the term antibody could be replaced by receptor, binding molecule, or binding agent throughout the specification without the loss of meaning. The term antigen derivative could likewise be replaced by analyte analog or another term that denotes a functional substitute of the target susbstance. The scope of this disclosure is intended to cover all of these substitutions.

The device includes a sample collection pad with a first end and a second end. The sample collection pad is adapted for absorbing oral fluid. The device also includes a holder with a front-end, a middle, and a rear end. The front end of the holder removably holds the second end of the sample collection pad with the first end of the sample collection pad protruding from the holder for absorbing the oral fluid in a first configuration. The device further has a flexible cap with a first end portion spaced from the sample collection pad and a second end supported on the holder in the first configuration. The device has a second configuration in which the sample collection pad has been pulled and moved relative to the holder.

The test device and method can advantageously include the sample collection pad being gripped between inner walls of the cap by a pinching action and moved into the second configuration. The sample collection pad can be left in the cap and the cap can be replaced on the holder for protection of the sample collection pad in the second configuration.

The holder has at least one channel extending from the front end through the middle and into the rear end the holder. The holder retains the second end of the sample collection pad in contact with a sample transfer pad and the sample transfer pad in contact with a conjugate pad. The conjugate pad has a colored antibody conjugate of the antigen so that a reaction will occur when the antigen in the sample passes through the conjugate pad. An antigen derivative carrying membrane has first and second ends and the conjugate pad is held in contact with the first end of the membrane. In this case the antigen derivative is an immobilized deposit of the antigen or a derivative of the antigen. An absorbent member with first and second ends has its first end held in contact with the second end of the membrane. Each of the sample transfer pad, the conjugate pad, the membrane, and the absorbent member are held in the at least one channel of the holder and form a wicking path through which a sample fluid migrates by capillary action.

It is to be understood that the positioning of the antigen derivatives and the antibodies can be reversed. That is, the antibodies can be immobilized on the membrane and the antigen derivatives can be colored and movably placed on the conjugate pad.

The holder of the test device preferably has a recess in the middle and at least one window disposed in the recess. The window is for viewing the effects of chemical reactions within the holder and for data collection via the window by sight. While the recess is not necessary, the recess facilitates data collection by a camera or a reader brought into the recess in close proximity to the effects of the chemical reactions.

One or more elements including the sample transfer pad, the conjugate pad, and the sample collection pad of the test device has a surfactant to facilitate wicking of oral fluid through the elements.

By way of example and not by way of limitation, the test device has an analytical sensitivity enabling detection of a substance in concentrations less than or equal to 500 ng/mL in order to be effective in detecting some of the antigens in oral fluid. Another exemplary threshold concentration is 50 ng/mL or less. For other antigens, an analytical sensitivity of the device enables detection of the substances in concentrations of less than or equal to 5 ng/mL.

The test device may be more generally used for sample fluids other than oral fluid. That is, the test device can be used for urine, blood, or other fluids. Furthermore, as set forth above, the test device may be utilized for detecting target substances other than antigens. That is, the test device may be used for determining a presence of any of a variety of substances in a body fluid. Still the device can advantageously integrate a prescreen test and a confirmation test sample collection with the single device by a single sample collection. In the more general case of testing other sample fluids, the test device still has the sample collection pad, the holder, and the various elements that form the wicking path as set forth above. However, the antigen derivative on the membrane may be replaced by any target substance or derivative thereof, and the colored antibody may be replaced by a corresponding conjugate reagent of the target substance.

The method of testing according to the invention includes an initial step of sampling by soaking the sample collection pad with a sample of the body fluid. Next the step of prescreen testing the sample is performed by permitting movement of a fluid of the sample to migrate along a wicking path from the sample collection pad through the conjugate pad and into the membrane. When a sufficient amount of the sample has been collected, the fluid migration is stopped in order to thereby retain a sufficient confirmation sample in the sample collection pad. This is achieved by separating the sample collection pad from the wicking path after sampling and prescreen testing. This can be advantageously implemented while migration is in the front to rear direction in order to avoid any possibility of backflow. Then the sample collection pad is stored for subsequent confirmation testing on the confirmation sample retained in the sample collection pad.

The holder advantageously has a socket that removably holds the sample collection pad in the first configuration. The device further includes a cap for enclosing the sample collection pad on the holder. The holder also holds a sample transfer pad between the sample collection pad and the membrane. As such, the step of stopping the migration further includes pinching the sample collection pad between inner walls of a cap and pulling the sample collection pad out of contact with the sample transfer pad. While simply separating the sample collection pad from the sample transfer pad and the wicking path is generally sufficient, this step may further include pulling the sample collection pad out of a socket of the holder to place the device in the second configuration.

The step of storing can include leaving the collection pad in a first portion of the cap, placing the cap back on the testing device, and sealing the cap on the testing device with a tamper resistant tape.

When the sample fluid is oral fluid, then the step of sampling can further include placing the device in a person's mouth for a predetermined length of time so that the sample collection pad absorbs oral fluid. By way of example and not by way of limitation, a range from 1 to 20 minutes in a person's mouth should be sufficient although longer or shorter periods of time may be needed depending on the absorbent materials utilized in the device and the specific tests being run. A further and continuous aspect of the method is the monitoring during collection, prescreen testing and storing of the confirmation sample.

Further by way of example and not by way of limitation, the method of using also includes initially detecting a antigen concentration of 500 ng/mL or less in the prescreen testing for some applications. Furthermore, by way of example only, the method includes the step of detecting a antigen concentration of 5 ng/mL or less in the prescreen testing, which is required for some antigens in oral fluid.

As can be appreciated from the above description, the only equipment that the sample needs to contact prior to confirmation testing is the device itself including the sample collection pad and the holder. Furthermore, the only necessary human contact with the sample for an oral fluid sample is that of the person's mouth from which the sample is being taken. The test device can replace the alternative lateral flow immunoassay urinalysis and thus overcome the normally negative human responses to handling urine.

The test device also helps to overcome the other drawbacks associated with urinalysis. That is, the test device, when used in an oral fluid sample application, does not require any privacy during sample collection. Therefore, the person being tested and the device can be monitored continuously during sample collection and prescreen testing. This aspect of the invention enables complete prevention of adulteration and contamination of the sample. Furthermore, there is no requirement for the attendant to be of the same sex as the person being tested. Hence, overall costs of retesting and additional personnel are reduced.

In order for testing and analysis of oral fluid samples to be a viable alternative to urinalysis or other tests, the instant invention implements features to overcome the historical drawbacks associated with oral fluid samples and testing. That is, the instant device utilizes surfactants and other chemicals to deal with the viscous nature of oral fluid. Furthermore, the device further has increased sensitivity to deal with the substantially lower concentrations of antigens in oral fluid.

One of the advantages of utilizing oral fluid as a sample is that the constituents in oral fluid may more closely resemble the dynamic chemical concentrations in the blood as opposed to traditional urine samples in which the kidneys act to filter out relatively large amounts of impurities. In this way, the oral application of the test device and method may overcome the drawback of the presence of nonrepresentative amounts of some antigens in urinalysis testing.

The instant device and method further overcome the need for large sample containers and large sample sizes. This is because the sample is carried to the sites of chemical reactions, (immobilized indicator lines), by wicking. A sufficient amount of the sample can be left in the sample collection pad for confirmation testing. The sufficient amount of the sample is preserved by moving the sample collection pad into the second configuration. These features of the test device also overcome the drawbacks and need for dipping, ladling, and pouring, which generally involve additional equipment and increase the chances of contamination of the sample.

The test device likewise overcomes the drawbacks of dipsticks and similar devices that introduce reagents into the sample. The instant test device obviates any need for such introduction, which might taint the sample. In fact, the instant device and method have a means for preventing back flow of a portion of the sample that has been prescreen tested. This means for preventing is provided by separating the sample collection pad from the wicking path, which provides an untainted portion of the sample for confirmation testing. Indeed the instant device and method overcome the drawbacks of requiring several pieces of equipment and several steps. That is, the instant device automatically collects a sample and performs a prescreen test while simultaneously providing for storing an untainted portion of the sample for confirmation testing.

Overall, the instant device is provided by an apparatus that can be made compact, and yet has the capability of identifying a multitude of antigens by the single device. The device implements this device as probe that emulates an oral thermometer. That is, the device is placed in a mouth of a person to be tested and left for a period of time in order to absorb oral fluid. The prescreen test runs automatically as the oral fluid migrates along a wicking path. Any antigens present in the oral fluid combine with a mobile colored antibody provided in the path and the antibody is unavailable to bond with an immobilized deposit of the antigen derivative downstream. When a given antigen is not present in the sample, the corresponding colored antibody is carried to the immobilized deposit of the antigen derivative at a specific position on a test strip membrane by the wicking.

Here the antibody bonds to the immobilized antigen derivative in a concentrated mass. The test strip can then be read through a window of the device. A plurality of deposits of immobilized deposits and a plurality of test strip membranes can be provided in a device that is still compact enough to fit in a person's mouth for sample collection.

The antibodies and immobilized antigen derivatives can include any combination of substances that were in the sample prior to the time of testing and any adulterant substances that may be added at the time of testing. Intentional adulteration is more easily achieved during conventional urinalysis since the subject person may not be monitored during sampling. The test device enables constant monitoring during sampling and the prescreening test by way of an immunoassay of oral fluid. It is difficult, if not dangerous, for a subject person to attempt to adulterate an oral fluid sample. However the test device and method can be used on other body fluids. In any case, the instant device overcomes the deficiencies of the past by an apparatus that can handle detection of multiple antigens and adulterants with a single compact device.

The invention, now having been briefly summarized, may be better visualized by turning to the following drawings wherein like elements are referenced by like numerals.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS

For purposes of clarity the target substances are referred to herein by the exemplary term antigens, the substances placed in the device for simulating the antigens are referred to as antigen derivatives, and the substances that are conjugates of the antigens and antigen derivatives are referred to as antibodies. It is to be expressly understood that the terms antigen/antibody refer to a particular type of target substance and its binding conjugate. However, the term antigen could be replaced by analyte, target substance; or ligand, and the term antibody could be replaced by receptor, binding molecule, or binding agent throughout the specification without the loss of meaning. The term antigen derivative could likewise be replaced by analyte analog or anther term that denotes a functional substitute of the target susbstance. In fact, the scope of this disclosure is intended to cover all of these substitutions.

Figure 1:
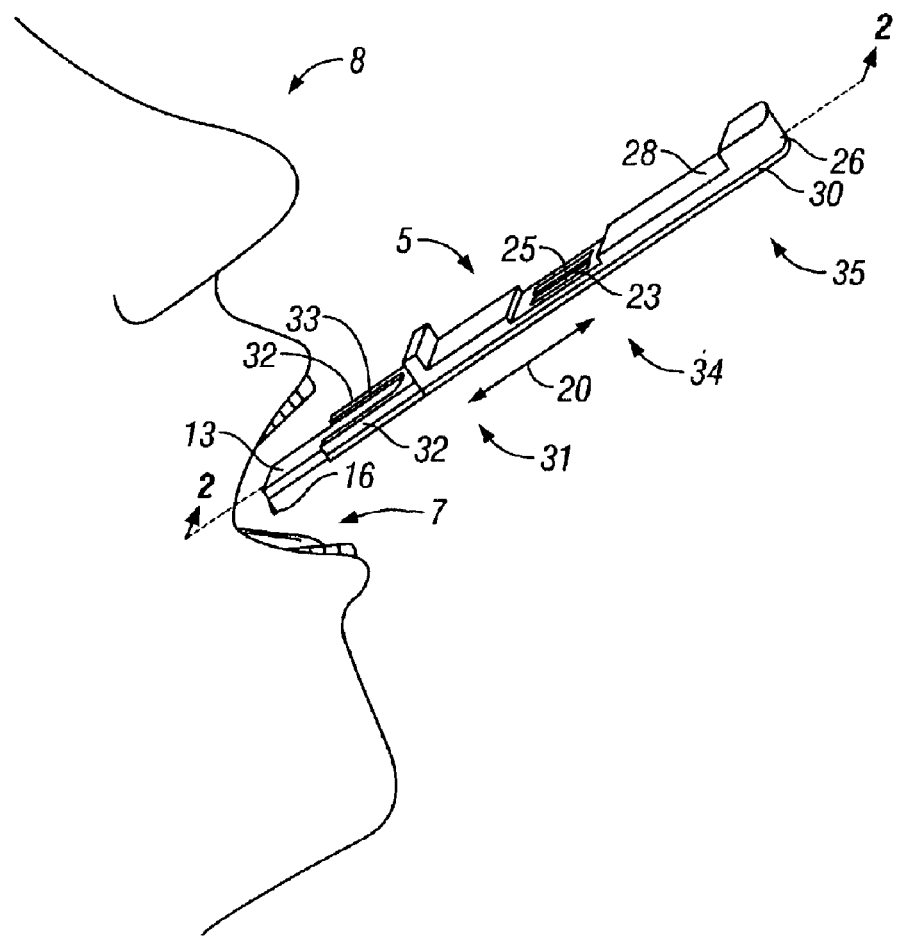
FIG. 1 is a perspective view of the test device depicting placement and removal from the person's mouth.

A preferred embodiment of the test device is illustrated in FIG. 1 and designated generally by the referenced numeral 5, which is a chemical contact test device that utilizes lateral flow of a fluid sample. The test device 5 is adapted to be placed in the mouth 7 of a person 8. As shown, a sample collection pad 13 is inserted to absorb oral fluid 16 from a person's mouth 7. As indicated by a double-headed arrow 20, FIG. 1 also depicts removal of the test device 5 from the person's mouth 7. While in accordance with the instant invention the device can be implemented with different sample body fluids, in the preferred embodiment, the sample is oral fluid 16. As depicted in FIG. 1, the device 5 can be utilized in a fashion similar to placement and removal of an oral thermometer.

The test device 5 is preferably placed in the person's mouth for one to twenty minutes during which time oral fluid 16 is absorbed through the sample collection pad 13. Simply stated, antigens in the oral fluid react with their antibodies during wicking such that the antibodies are thereby prevented from further reaction with immobilized, predisposed antigen derivatives located in windows 23, 25 of the device 5. On the other hand, if no antigen is present in the oral fluid 16, then the antibodies are free to react with the immobilized, previously disposed antigen derivatives and the results of the reaction(s) can be viewed through the windows 23, 25.

As shown in FIG. 1, the device 5 comprises a holder 26 made up of an upper piece 28 and a lower piece 30. The holder 26 generally has a front-end 31 including supports 32 that generally help maintain the shape of the sample collection pad 13. The supports 32 define a U-shaped recess 33 therebetween. This recess 33 has the advantage of permitting engagement of the sample collection pad 13 between the supports 32 to allow exposure to saliva and easy removal of the pad 13. The holder 26 further has a middle 34 and a rear end 35.

Figure 2A:
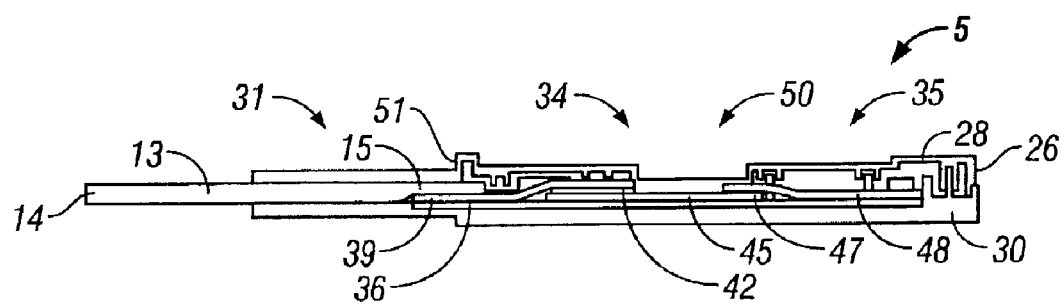
FIG. 2A is a cross-sectional view taken along lines 2—2 of FIG. 1.

FIG. 2A shows the internal elements that enable wicking of the oral fluid 16. A backing 36 holds various other elements together. Namely, a sample transfer pad 39, a conjugate pad 42, a membrane 45 having a front-end 46 and the rear end 47, and an absorbent member 48. Each of these elements contacts at least one other of the elements to form a continuous path for wicking of the oral fluid 16. Each of the sample collection pad 13, the sample transfer pad 39, the conjugate pad 42, and the absorbent member 48 comprise any of a variety of absorbent materials suitable for chemical testing of body fluids. The membrane 45 may comprise a nitrocellulose membrane strip or an equivalent. The sample collection pad 13 is also in contact with the most upstream of these elements and forms a part of the wicking path. The sample collection pad 13 includes a first end 14 and a second end 15.

The oral fluid 16 is absorbed by the sample collection pad 13 and is wicked from the front end 31 toward the rear end 35 of the device 5. A second end 15 of the sample collection pad 13 contacts the sample transfer pad 39 in an overlapping relationship. The sample transfer pad 39, in turn, contacts the conjugate pad 42 in an overlapping relationship. The conjugate pad 42 rests on a first end 46 of the membrane 45. Wicking continues through the membrane 45 to a second end 47 of the membrane 45 that is overlapped by the absorbent member 48. The absorbent member 48 acts as a moisture sink to further draw the fluid sample rearwardly in the test device 5 by capillary action.

Figure 2B:
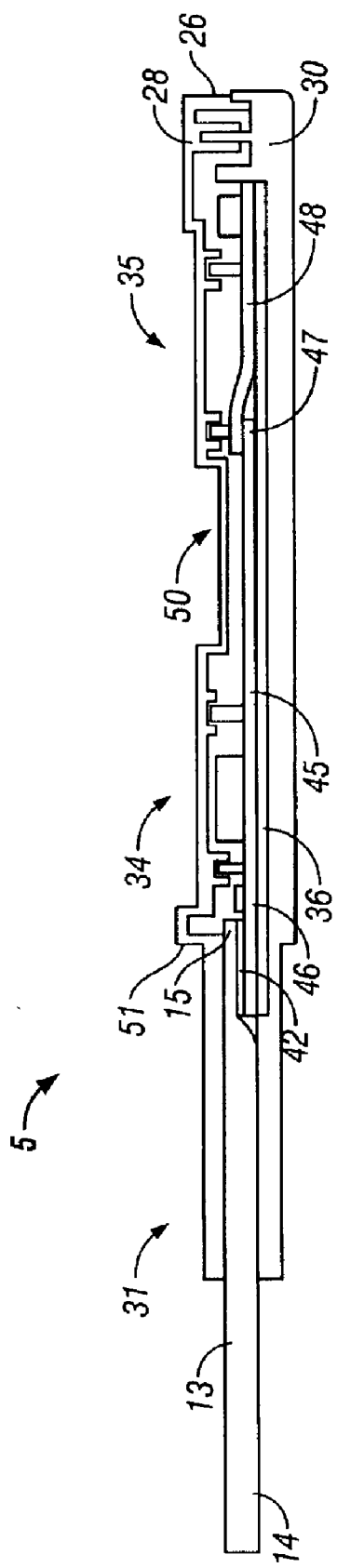
FIG. 2B is a cross-sectional view taken along lines 2—2 of FIG. 1 depicting an alternative embodiment.
Figure 2C:
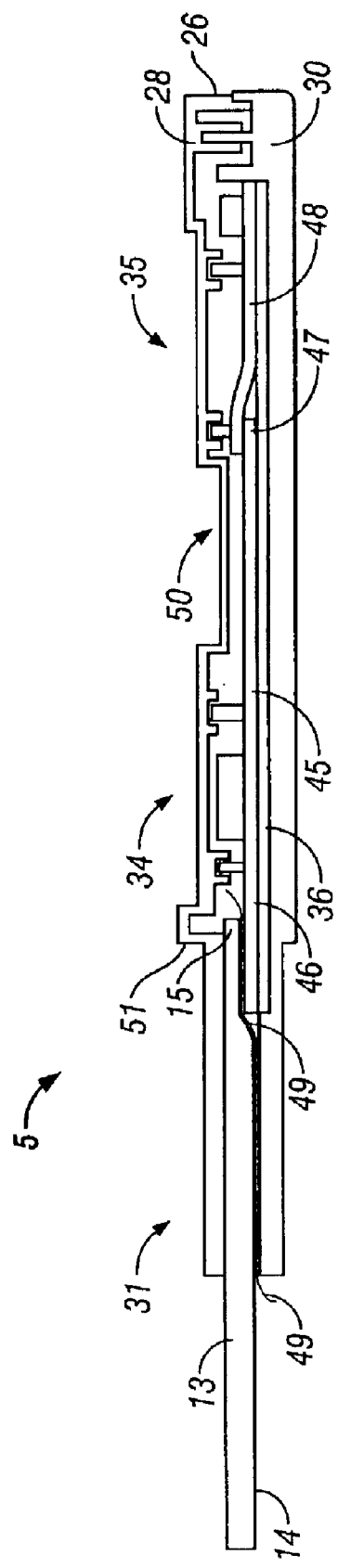
FIG. 2C is a cross-sectional view taken along lines 2—2 of FIG. 1 depicting a further alternative embodiment.

While the sample transfer pad 39 serves to transfer the sample fluid from the sample collection pad 13 to the conjugate pad 42 in the preferred embodiment, an alternative embodiment eliminates the sample transfer pad and has the sample collection pad 13 in direct contact with the conjugate pad 42 as shown in FIG. 2B. Similarly, the conjugate pad 42 can be eliminated and the one or more antibodies can be placed on the membrane 45 as shown in FIG. 2C. In this case, the antibodies are placed at the first end 46 of the membrane 45 to give the needed time for reaction with any antigens in the sample while migrating toward the immobilized deposits of the antigen derivatives further downstream on the membrane 45. Also shown in FIG. 2C is an optional shield 49 placed between the second end 15 of the sample collection pad 13 and the membrane 45. It is to be understood that such a shield 49 may be applied to any of the embodiments disclosed herein, and acts to stop migration of the sample fluid until the shield 49 is removed. This feature is important on tests in which a start time is critical. Also, for practical purposes it is often preferable to run the prescreen test after leaving the presence of the person 8 being tested. Thus, the shield 49 could be left intact until the person 8 being tested is no longer present.

Each of the elements forming the wicking path is selected based on its absorptive qualities and can be selected or modified to provide additional qualities. For example, each of the sample collection pad 13, the sample transfer pad 39, and the conjugate pad 42 has specific absorptive qualities. These pads 13, 39, 42 can be selected or modified to provide filtering of the sample. This may be important to prevent impurities, enzymes, or bacteria from interfering with the chemical reaction and thus the test results. On the other hand, these pads 13, 39, 42 can be selected or modified to further improve flow of the sample therethrough. This may be accomplished by the addition of any of a variety of surfactants and other chemicals with which one or more of the pads 13, 39, 42 may be treated. This likewise, can improve the capabilities of the test device in handling fluids that otherwise would have viscosities that are too high to permit proper migration by capillary action.

Another alternative embodiment entails swapping locations of the antibody and the previously disposed immobilized antigen derivative on the membrane 45. In this case, the antigen derivatives are colored and removably placed on the conjugate pad 42. Alternatively, the colored antigen derivatives can simply be placed upstream of the non-colored antibodies. In this case, the antibodies are immobilized on the membrane, and any antigens in the sample compete with the colored antigen derivatives removably placed upstream to react with the immobilized antibodies. As such, the intensity of the coloration at the immobilized antibody indicator lines enables accurate detection of the antigen levels in the sample.

In the preferred embodiment of FIG. 2A, the conjugate pad 42 comprises an absorbent member with a reagent composition disposed therein. The reagent composition is reactive with a certain antigen or chemicals, which may be found in the sample. The conjugate pad 42 can include one or more adulteration substance conjugates as reagent compositions to indicate whether the sample has been adulterated. However, in the preferred embodiment that utilizes an oral fluid sample, adulteration is more difficult. Indeed, a major benefit of the preferred embodiment of an oral test is that the test does not call for privacy during sampling, and the entire prescreen test can be monitored by a test administrator. On the other hand, the device in accordance with the instant invention may be applied with other samples such as with urine and still advantageously provide some of the same advantages as achieved in oral fluid collection and testing. In any case, the conjugate pad can include conjugates of certain adulterants that are not normal constituents of the sample being taken. Such constituents include but are not limited to bleach or glutaraldehyde. Alternatively, the conjugate pad can include a antibody of a normally present substance in the sample, but which antibody is included to detect an abnormal presence of the substance such as excessively high or excessively low levels. For example, an abnormally high level of creatinine may be the target for which a conjugate is provided in the conjugate pad.

In the preferred embodiment, the reagents in the conjugate pad include colored antibodies that are conjugates of the antigens in the samples to be analyzed. Preferably, the antibodies are removably disposed in the conjugate pad and are carried by the fluid of the sample in the direction of fluid migration during wicking. As such, the antibodies that have not undergone a reaction with an antigen in the sample are carried to and bond with the previously disposed and immobilized antigen derivatives in the membrane 45. It is to be understood that the previously disposed and immobilized antigen derivatives can be alternatively replaced by other reagents that react with the selected antibodies of the targeted antigens.

In the preferred embodiment, the sample oral fluid 16 migrating by wicking will carry antibodies of the targeted antigens from the colored antibody conjugate pad into the membrane 45. Here in a position 50 immediately below the windows 23, 25, the previously disposed and immobilized antigen derivatives will provide reactions with any remaining antibodies carried from the colored antibody conjugate pad 42. The antibodies are colored for easy visual detection when they react and bond to the previously disposed and immobilized antigen derivatives held at specific locations on the membrane 45.

Figure 3:
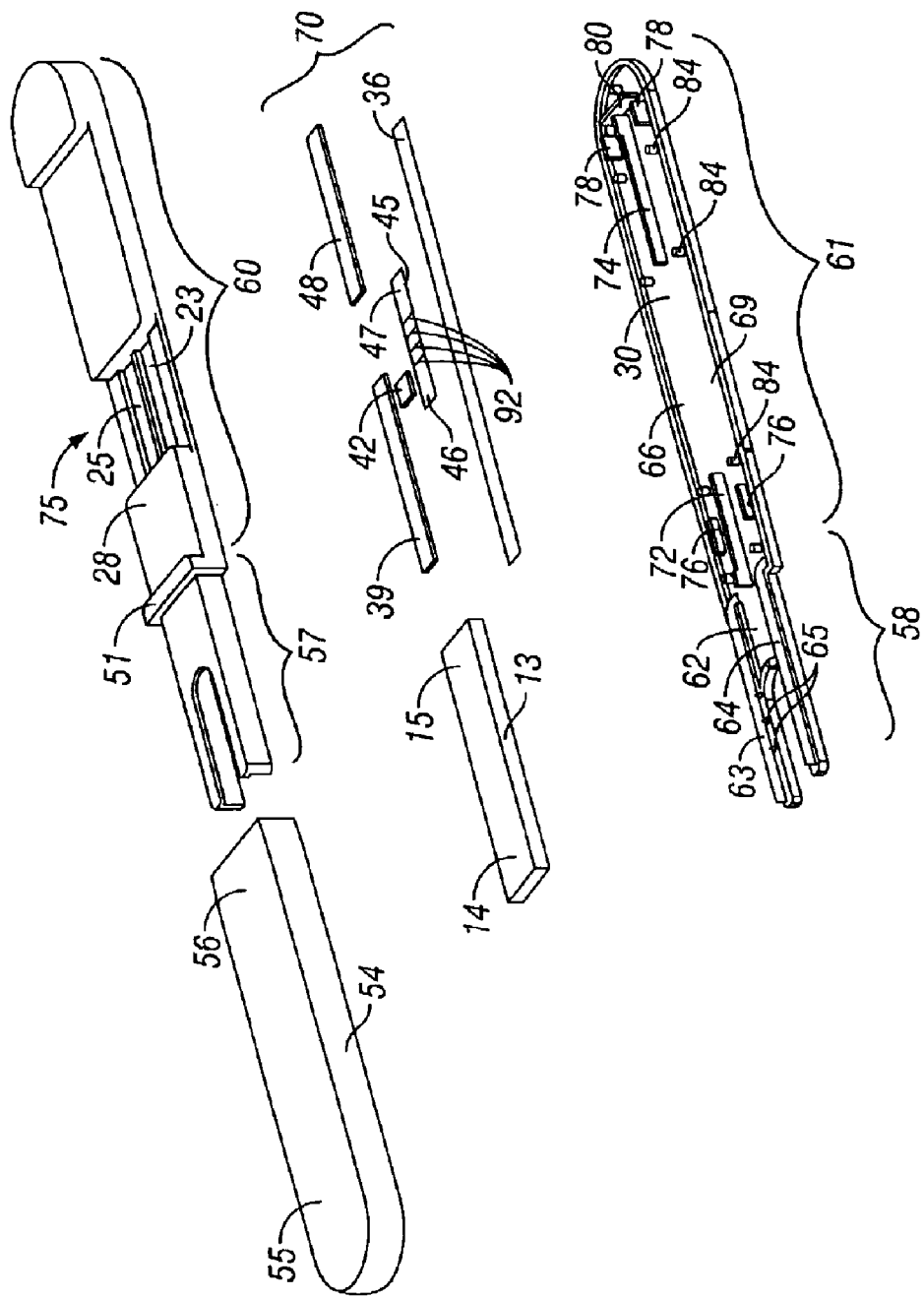
FIG. 3 is an exploded view of the test strip of FIGS. 1 and 2A, and including a cap.

FIG. 2A also shows a seat 51 that acts as a stop for a cap 54 shown in FIG. 3. The cap 54 has a front-portion 55 and a rear portion 56. Upper and lower holder pieces 28, 30 form respective upper and lower cap receiving portions 57, 58. When assembled, the holder 26 receives the cap 54 as indicated by arrows 59 shown in FIG. 5. The cap 54 may be transparent or translucent for viewing the contents or the configuration of the contents. Alternatively, the cap may be tinted or opaque to prevent light from damaging or affecting the sample and the test results. The upper and lower holder pieces 28, 30 also comprise upper and lower handle portions 60, 61.

The exploded view of FIG. 3 further shows how the pieces 28, 30, and the internal elements of the device 5 fit together. In FIG. 3, the windows 23, 25 are disposed in a recess 75 formed in the upper piece 28. specifically, the holder forms a sample collection pad support portion 62 for removably holding the sample collection pad 13 in overlapping relation to the sample transfer pad 39 during sample collection and prescreen testing. Walls 63, 64 on the lower piece 30 straddle the sample collection pad support portion 62 and engage mating structure on the upper piece 28 of the holder 26. Protrusions 65 on the tower piece 30 aid in retaining the sample collection pad 13 in the support portion 62. The sample collection pad support portion 62 generally spans an entire width of the holder 26.

On the other hand, the holder forms first and second channels 66, 69 that each span only a fraction of the width of the holder. The channels 66, 69 accommodate and hold respective assemblies 70 of elements for the prescreen testing. Only one assembly 70 is shown in FIG. 3. However, it is to be understood that the embodiment of FIG. 3 accommodates two such assemblies 70 in a side by side relationship of the device 5. Furthermore, it is contemplated that any number of the assemblies 70 can be similarly provided and assimilated into the device in accordance with the instant invention. In the preferred embodiment, dividing walls 72, 74 separate the holder into the first and second channels 66, 69. Outer walls 76, 78 prevent the assemblies 70 from moving outwardly. End wall 80 prevents the assemblies from moving rearwardly. Studs 84 on the lower piece 30 of the holder 26 engage mating structure on the upper piece 28 in a friction fit relationship that holds the pieces 28, 30 together in an assembled configuration.

The assembly 70 comprises the various elements that are needed for the prescreen test including the sample transfer pad 39, the colored antibody conjugate pad 42, the membrane 45, and the absorbent member 48. These elements are coupled to the backing 36 to form an integral unit therewith. These elements are also coupled to each other in the relationship set forth above to provide the wicking path for the oral fluid. FIG. 3 shows the previously disposed immobilized antigen derivative on the membrane 45 in the form of lines 92. It is to be understood that these lines 92 are generally not visible or at least are relatively colorless until the prescreen test has been run. The lines 92 will remain invisible or colorless after the prescreen test to the extent that corresponding antigens were present in the sample. That is, each antigen in the sample will react with a corresponding antibody in the colored antibody conjugate pad 42. The corresponding colored antibody that participates in the reaction will no longer be available to react with the immobilized antigen derivative located at a respective line 92. Hence, little or no colored antibody is left after reacting with the antigen in the sample, and little or no color will show up at a corresponding line 92.

Figure 4:
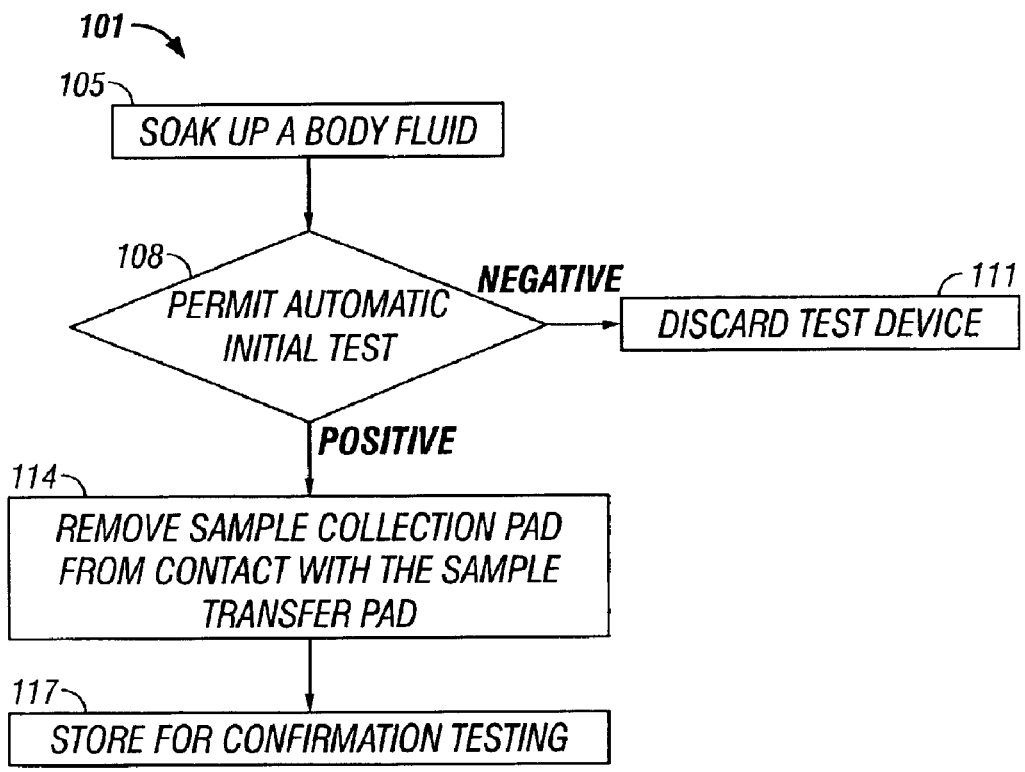
FIG. 4 is a flow diagram illustrating a preferred method of detecting a antigen in a sample.

FIG. 4 is a flow diagram showing the steps of a method 101 of testing for the presence of antigens in a body fluid sample. Firstly, the device is permitted to soak up a body fluid as shown at block 105. Next, and somewhat simultaneously, the prescreen test is permitted to proceed in accordance with block 108. This step occurs automatically as long as the sample fluid is permitted to wick through the essential elements of the device. If the results of the prescreen test are negative, then the device 5 is discarded and no further testing is necessary as indicated at 111. On the other hand, if any of the prescreen test results are positive, then a confirmation test is required. Thus, the sample collection pad 13 is separated from the rest of the wicking path to stop migration of the remainder of the sample in accordance with step 114. In this way, the remaining portion of the sample is preserved for confirmation testing. After this step 114 of removing the collection test pad, the sample collection pad is stored for confirmation testing in accordance with block 117. The method may further comprise the step of confirmation testing by at least one of gas chromatography and mass spectrometry.

The method of testing includes collecting a sufficient amount of the sample fluid to supply both the prescreen test and the confirmation test. As an example and not by way of limitation, a sufficient amount will normally be in the range of from 0.5 mL to 2.0 mL, for example. In the preferred embodiment, it has been found that approximately one mL is sufficient for this purpose. As such, the sample collection pad 13 must have sufficient capacity to absorb one mL of the sample. With a one mL sample, approximately 200 microliters are used up during prescreen testing. This leaves approximately 800 microliters for the confirmation test. It is to be understood that a larger or a smaller total sample than those specified above can be collected and utilized without departing from the spirit and scope of the instant invention.

Figure 5:
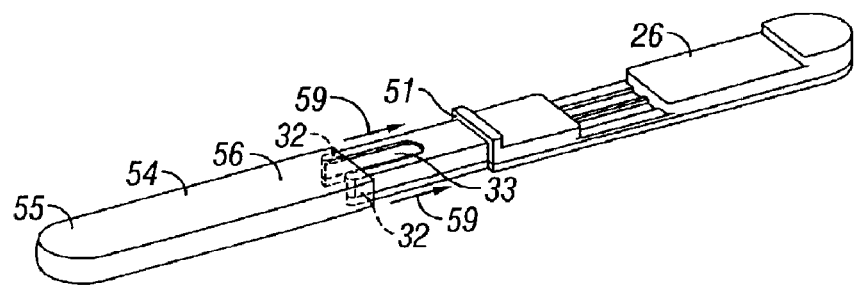
FIG. 5 is a perspective view of the test device depicting placement and replacement of the cap of the device on the holder.

FIG. 5 depicts the placement or replacement of the cap 54. Generally the cap 54 is placed on the holder by a force in the direction of the arrows 59 simply in order to protect the sample collection pad 13 against contamination. Another occasion in which the cap 54 is placed on the holder 26 is after the sample collection pad 13 has been removed. The sample collection pad 13 may be removed and stored separately from the device for subsequent confirmation testing. However, in the preferred method, the sample collection pad 13 is separated from the wicking path yet retained in the cap 54. In this case, the cap 54 may be replaced on the holder 26 with the sample collection pad therein. This method of storing the sample collection pad is advantageous because the chances of contamination are greatly reduced.

Figure 6:
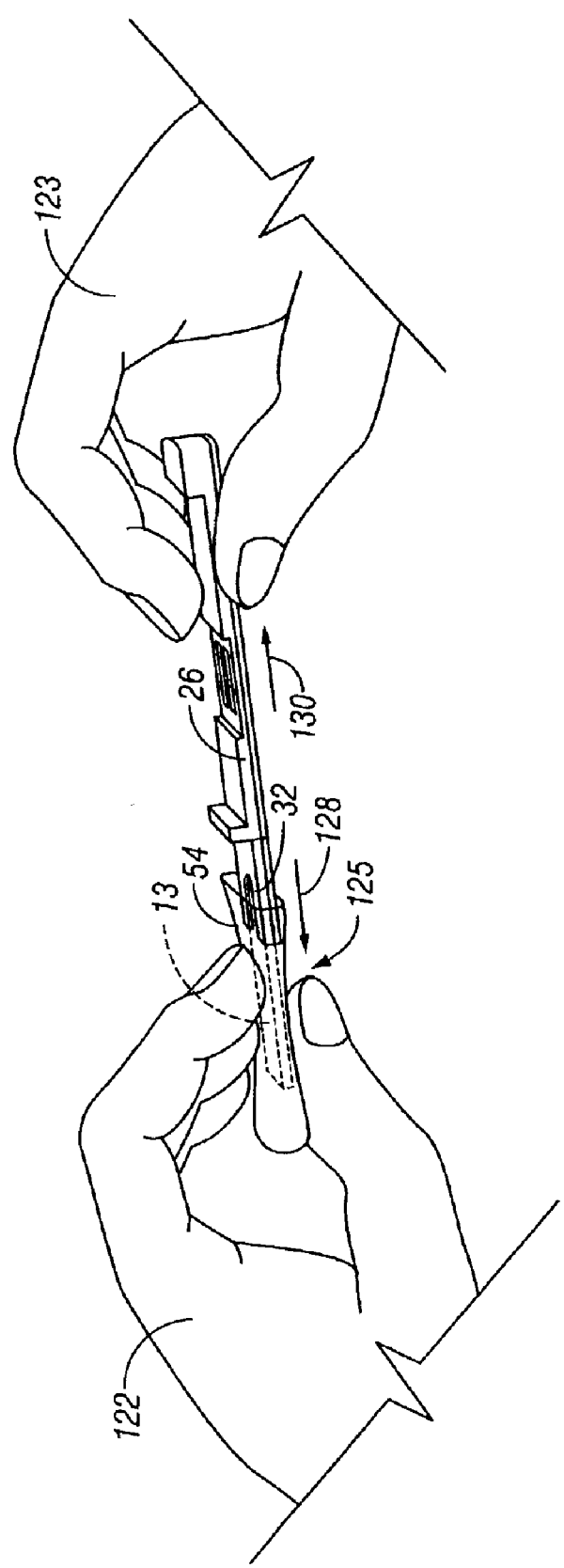
FIG. 6 is a perspective view showing pinching removal of the cap and sample collection pad of the test device.

While the removal of the sample collection pad can be implemented in any number of sanitary ways, the instant device and method advantageously provides an easy and efficient manner of doing so. This feature is depicted in FIG. 6 and greatly reduces the chances of contamination. FIG. 6 shows a user's hands 122, 123 pinching the cap 54 and the sample collection pad 13 between inner walls of the cap 54 at 125. While pinching the cap 54 and pad 13 a user pulls the cap 54 in the direction of the arrow 128 and simultaneously pulls the holder 26 in the direction of the arrow 130. This action separates the sample collection pad 13 from the wicking path and may be used to completely separate the sample collection pad 13 from the supports 32.

Figure 7:
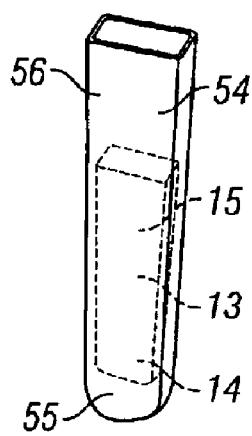
FIG. 7 is a perspective view of the removed cap and sample collection pad of the test device.
Figure 8:
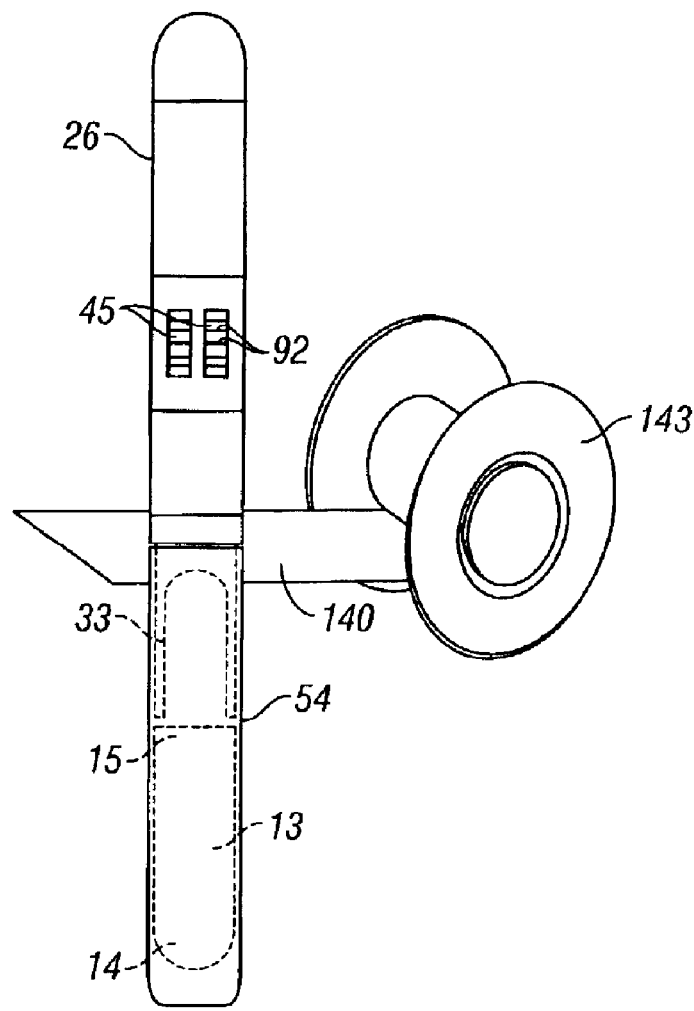
FIG. 8 is a top plan view showing storing of the sample collection pad in the cap for subsequent confirmation testing.

FIG. 7 shows the sample collection pad inside the cap 54. As shown, the sample collection pad 13 has been permitted to fall into the first portion 55 of the cap. Then the cap 54 is replaced onto the holder and a tamperproof tape 140 from a tape roll 143 is used to secure the cap 54 to the holder 26 as shown in FIG. 8. In the exemplary depiction of FIG. 8, a positive test has resulted for one of eight lines 92. That is, one of the lines 92 remains invisible or non-colored. Thus, FIG. 8 shows a typical case in which a confirmation test would be required. As shown in FIGS. 3 and 8, four lines 92 are provided on each of the membrane strips 45. One of these lines 92 on each of the membrane strips 45 is a control to assure the test administrator that the device is functioning properly during testing. Thus, for example, the device can test for up to 6 antigens. Some of these antigens can be adulterants, or they may all be drugs or metabolites of drugs to be detected. Any number of additional lines within reason may be added to the membrane strips 45 so that a multitude of antigens can be detected. Alternatively or additionally, more channels can be provided to receive additional assemblies with further additional lines.

It can be appreciated that with the instant device and method, the only contact with the sample collection pad is with the holder 26, the cap 54, and the mouth 7 or sample from the person 8 being tested. This minimal contact can be limited to take place only in the presence of the test administrator, and any additional chance of contamination of the sample prior to confirmation testing can be avoided.

It is to be expressly understood that the reagent composition can be located in the membrane as an immobilized deposit of a conjugate binding partner of the antigen and antigen derivative. In this case, the antigen derivative can be located in the conjugate pad as a movable colored antigen derivative to be carried by the sample to the immobilized conjugate binding partner.

As set forth above, the antigen/antibody used throughout the description above is a specific example of a broader concept in which the term antigen is replaced by the general term analyte and the term antibody is replaced by receptor. Examples of analytes are a drug, a hormone, an antigen, a hapten, a lectin, an apoprotein, or a cofactor. More specific examples are drug metabolites, for example cotinine as a marker of nicotine use, or a hormone such as human chorionic gonadotropin (HCG) as a marker of pregnancy. While the instant invention has particular application in the field of drug screening and is especially useful for detecting use of drugs of abuse for determining employability or for determining drug use status of a parolee, the device and method are or may be useful in many other applications as well. For example, the conjugate pad 42 may also comprise a bodily substance detection pad having a reagent composition or compositions to detect bodily substances such as glucose, bilirubin, ketone, blood, protein, urobilinogen, nitrite, leucocytes and more. Of particular interest are target substances that will permit identification of infectious diseases, therapeutic drugs, cancer markers, and cardiac markers. The bodily substance detection pad may also measure pH and specific gravity of the sample. Detection of these additional substances has great potential for diagnosing diseases or predicting future health.

Many alterations and modifications may be made by those having ordinary skill in the art without departing from the spirit and scope of the invention. Therefore, it must be understood that the illustrated embodiments have been set forth only for the purposes of example and that it should not be taken as limiting the invention as defined by the following claims. The claims are thus to be understood to include what is specifically illustrated and described above, what is conceptionally equivalent, what can be obviously substituted and also what incorporates the essential idea of the invention.

What is claimed is:

1. A test device for determining a presence of an analyte in a body fluid, the device integrating a prescreen test and a confirmation test sample collection with the device, the device comprising:
   a sample collection pad, the sample collection pad having a first end and a second end, the sample collection pad being adapted for absorbing the body fluid;
   a holder having a front-end, a middle, and a rear end, the front end of the holder removably holding the second end of the sample collection pad with the first end of the sample collection pad protruding from the holder for absorbing the body fluid;
   a flexible cap, the cap having a first end and a second end, the second end of the flexible cap supported on the holder;
   wherein the sample collection pad is movable relative to the holder between a first configuration in which the sample collection pad has not been moved and a first portion of the cap is spaced from the sample collection pad, and a second configuration in which the sample collection pad has been pulled and moved relative to the holder; and
   wherein the sample collection pad is gripped between inner walls of the cap by a pinching action and moved into the second configuration, the sample collection pad remaining in the cap with the cap replaced on the holder for protection of the sample collection pad in the second configuration.

2. The test device of claim 1, wherein the analyte is one of a drug, a hormone, an antigen, an antibody, a hapten, a lectin, an apoprotein, or a cofactor.

3. A test device for determining a presence of an analyte in a body fluid, the device integrating a prescreen test and a confirmation test sample collection with the device, the device comprising:
   a sample collection pad, the sample collection pad having a first end and a second end, the sample collection pad being adapted for absorbing the body fluid;
   a holder having a front-end, a middle, and a rear end, the front end of the holder removably holding the second end of the sample collection pad with the first end of the sample collection pad protruding from the holder for absorbing the body fluid;
   a flexible cap, the cap having a first end and a second end, the second end of the flexible cap supported on the holder;
   wherein the sample collection pad is movable relative to the holder between a first configuration in which the sample collection pad has not been moved and a first portion of the cap is spaced from the sample collection pad, and a second configuration in which the sample collection pad has been pulled and moved relative to the holder; and wherein the cap has a hollow volume in the first portion sized to receive the sample collection pad after separation of the sample collection pad from the holder, the second configuration comprising a separation of the sample collection pad from the holder.

4. The test device of claim 3, comprising a socket in the front end of the holder removably holding the sample collection pad, wherein the socket is surrounded by a seat that removably supports the cap.

5. The test device of claim 3, further comprising the holder having a window in the middle for viewing the effects of chemical reactions within the holder and for data collection via the window by a camera or reader brought in close proximity to the effects.

6. A test device for determining a presence of an analyte in a body fluid, the device integrating a prescreen test and a confirmation test sample collection with the device, the device comprising:
   a sample collection pad, the sample collection pad having a first end and a second end, the sample collection pad being adapted for absorbing the body fluid;
   a holder having a front-end, a middle, and a rear end, the front end of the holder removably holding the second end of the sample collection pad with the first end of the sample collection pad protruding from the holder for absorbing the body fluid;
   the holder having at least one channel extending from the front end through the middle and into the rear end of the holder;
   the at least one channel retaining the second end of the sample collection pad in contact with a sample transfer pad and the sample transfer pad in contact with a conjugate pad, the conjugate pad having a colored receptor thereon;
   a membrane having first and second ends, the conjugate pad held in contact with the first end of the membrane, the membrane having immobilized analyte analog deposits thereon;

an absorbent member having first and second ends with the first end of the absorbent member held in contact with the second end of the membrane; and a flexible cap, the cap having a first end and a second end, the second end of the flexible cap supported on the holder;

wherein the sample transfer pad, the conjugate pad, the membrane, and the absorbent member are wicking path elements held in the at least one channel of the holder; and wherein the sample collection pad is movable relative to the holder between a first configuration in which the sample collection pad has not been moved and a first portion of the cap is spaced from the sample collection pad, and a second configuration in which the sample collection pad has been pulled and moved relative to the holder.

7. The test device of claim 6, the at least one channel being a first of a plurality of channels, each channel holding wicking path elements similar to those disposed in the first channel and being in wicking communication with the sample collection pad during sample collection and prescreen testing, and wherein each membrane has a plurality of different analyte analogs for competitive reactions with a variety of respective receptors movably disposed upstream in each conjugate pad and carried to the analyte analogs by the body fluid.

8. The test device of claim 6, wherein at least one of the sample transfer pad, the conjugate pad, and the sample collection pad includes a surfactant to facilitate wicking of the body fluid through the wicking path elements.

9. A test device for determining a presence of an analyte in a body fluid, the device integrating a prescreen test and a confirmation test sample collection with the device, the device comprising:

a sample collection pad, the sample collection pad having a first end and a second end, the sample collection pad being adapted for absorbing the body fluid;

a holder having a front-end, a middle, and a rear end, the front end of the holder removably holding the second end of the sample collection pad with the first end of the sample collection pad protruding from the holder for absorbing the body fluid;

the holder having at least one channel extending from the front end through the middle and into the rear end of the holder;

the at least one channel retaining the second end of the sample collection pad in contact with a sample transfer pad and the sample transfer pad in contact with a conjugate pad, the conjugate pad having a colored analyte analog thereon;

a membrane disposed in the at least one channel and having first and second ends, the conjugate pad, held in contact with the first end of the membrane, the membrane having immobilized receptor deposits thereon;

an absorbent member disposed in the at least one channel and having first and second ends with the first end of the absorbent member held in contact with the second end of the membrane; and a flexible cap, the cap having a first end and a second end, the second end of the flexible cap supported on the holder;

wherein the sample transfer pad, the conjugate pad, the membrane, and the absorbent member are wicking path elements held in the at least one channel of the holder; and wherein the sample collection pad is movable relative to the holder between a first configuration in which the sample collection pad has not been moved and a first portion of the cap is spaced from the sample collection pad, and a second configuration in which the sample collection pad has been pulled and moved relative to the holder.

10. A test device for determining a presence of a substance in a body fluid, the device integrating a prescreen test and a confirmation test sample collection with the device, the device comprising:

a sample collection pad, the sample collection pad having a first end and a second end, the sample collection pad being adapted for absorbing a sample of the body fluid;

a holder having a front-end, a middle, and a rear end, the front end of the holder removably holding the sample collection pad with the first end of the sample collection pad protruding from the holder for absorbing the body fluid sample, the holder retaining a second end of the sample collection pad in contact with a sample transfer pad which in turn is held in contact with a conjugate pad, the sample collection pad remaining in contact with the sample transfer pad during sampling and prescreen testing, the conjugate pad having absorbent properties for causing migration of the sample from the sample collection pad toward the conjugate pad;

a membrane having first and second ends, the first end of the membrane being held by the holder in contact with the conjugate pad and having absorbent properties for causing migration of the body fluid from the sample pad toward the second end, the membrane having at least one of an analyte analog or a receptor on the membrane at a preselected location;

the holder having structure defining an opening through which the membrane and a colored conjugate of the analyte analog or receptor may be viewed;

the holder having a cap, the cap having a first end portion held in spaced relation to the first end of the sample collection pad in a first configuration, the cap having a second end portion supported on the holder; and means for separating the sample collection pad from the sample transfer pad, the conjugate pad, and the membrane to provide a second configuration.

11. The test device of claim 10, wherein the means for separating comprises a means for placing the sample collection pad in the first end portion of the cap without touching or contaminating the sample collection pad.

12. The test device of claim 10, further comprising the cap being inwardly flexible in at least one direction transverse to an axis through the first and second end portions of the cap.

13. The test device of claim 12, the cap having a hollow volume in the first end portion sized to receive the sample collection pad after removal and separation of the sample collection pad from the holder.

14. The test device of claim 10, further comprising an absorbent member in contact with a second end of the membrane and extending into the rear end of the holder to act as a sink for moisture from the sample.

15. The test device of claim 14, wherein the holder is hollow and surrounds and holds the sample collection pad, the sample transfer pad, the conjugate pad, the membrane, and the absorbent member in their relative positions.

16. The test device of claim 10, wherein the holder comprises a long narrow housing with a socket at one end receiving the sample collection pad.

17. The test device of claim 16, wherein the socket is surrounded by a seat that removably supports the cap.

18. The test device of claim 10, wherein the holder has a window in the middle corresponding in position to the preselected locations of the analyte analog or receptor on the membrane such that a camera or a reader may be brought into close proximity to the preselected locations on the membrane after sampling and prescreen testing for accurate analysis of test results.

19. A method for detecting a substance in a body fluid, the method comprising:

absorbing a sample of the body fluid with a sample collection pad;

prescreen testing the sample by permitting a fluid of the sample to migrate along a wicking path from the sample collection pad through a conjugate pad and into a membrane;

stopping the migration and thereby retaining a confirmation sample in the sample collection pad by separating the sample collection pad from the wicking path after absorbing and prescreen testing; and storing the sample collection pad for subsequent confirmation testing on the confirmation sample retained therein.

20. The method of claim 19, the step of stopping the migration further comprising:

pinching the sample collection pad between inner walls of a cap; and pulling the sample collection pad out of contact with a sample transfer pad.

21. The method of claim 19, further comprising the step of continuously monitoring the membrane during the steps of absorbing the sample, prescreen testing, stopping the migration, and storing the sample collection pad.

22. The method of claim 19, wherein the step of storing further comprises:

leaving the collection pad in a first end portion of the cap;

placing the cap back on the testing device; and sealing the cap on the testing device with a tamper resistant tape.

23. The method of claim 19, wherein the body fluid is oral fluid, and the step of absorbing further comprises placing the device in a person's mouth so that the sample collection pad absorbs oral fluid.

24. The method of claim 19, further comprising the step of confirmation testing by at least one of gas chromatography and mass spectrometry.

25. A method for detecting a substance in a body fluid, the method comprising:

absorbing a sample of the body fluid with a sample collection pad;

directing the sample from the sample collection pad through a conjugate pad and into a membrane by capillary action;

testing a portion of the sample by contact chemical means in the conjugate pad and membrane; and stopping a migration of the sample and thereby retaining a confirmation sample in the sample collection pad by separating the sample collection pad from a wicking path after absorbing and testing.

26. A test device for determining a presence of an analyte in a body fluid, the device integrating a prescreen test and confirmation test sample collection with the device, the device comprising:

a sample collection pad adapted for absorbing the body fluid;

a holder removably holding the sample collection pad with a portion of the sample collection pad protruding from the holder for absorbing the body fluid; and a flexible cap selectively seated on the holder;

wherein the pad is movable between a first configuration in which the sample collection pad has not been moved in the holder and a second configuration in which the sample collection pad has been pulled and moved relative to the holder; and wherein the sample collection pad is gripped between inner walls of the cap by a pinching action and moved into the second configuration, the sample collection pad remaining in the cap with the cap replaced on the holder for protection of the sample collection pad in the second configuration.

27. The test device of claim 26, further comprising the holder having a recess in a middle portion and at least one window disposed in the recess for viewing the effects of chemical reactions within the holder and for data collection via the window by a camera or reader brought into the recess in close proximity to the effects.

28. The test device of claim 26, further comprising:

the holder having at least one channel extending from a front end through a middle portion and into a rear end of the holder;

the holder retaining the sample collection pad in fluid communication with a conjugate pad in the first configuration, the conjugate pad having one of a receptor or an analyte analog thereon, and wherein the one of the receptor or the analyte analog on the conjugate pad is colored;

a membrane having first and second ends, the conjugate pad held in contact with the first end of the membrane, the membrane having the other of the receptor or the analyte analog; and an absorbent member having first and second ends with the first end of the absorbent member held in contact with the second end of the membrane; and wherein the conjugate pad, the membrane, and the absorbent member are held in the at least one channel of the holder.

29. The test device of claim 28, wherein at least one of the conjugate pad and the sample collection pad includes a surfactant to facilitate wicking of the body fluid through the device.

30. The test device of claim 28, wherein the analyte and analyte analog are one of a drug, a hormone, an antigen, an antibody, a hapten, a lectin, an apoprotein, or a cofactor and the receptor is a binding conjugate of the analyte and the analyte analog.

* * * * *